(12) United States Patent
Suzuki

(10) Patent No.: US 12,394,518 B2
(45) Date of Patent: Aug. 19, 2025

(54) INFORMATION PROCESSING SYSTEM, INFORMATION PROCESSING METHOD, AND NON-TRANSITORY COMPUTER READABLE MEDIUM

(71) Applicant: KANEKA CORPORATION, Osaka (JP)

(72) Inventor: Shohei Suzuki, Osaka (JP)

(73) Assignee: KANEKA CORPORATION, Osaka (JP)

( * ) Notice: Subject to any disclaimer, the term of this patent is extended or adjusted under 35 U.S.C. 154(b) by 161 days.

(21) Appl. No.: 18/354,830

(22) Filed: Jul. 19, 2023

(65) Prior Publication Data

US 2023/0360788 A1 Nov. 9, 2023

Related U.S. Application Data

(63) Continuation of application No. PCT/JP2021/038179, filed on Oct. 15, 2021.

(30) Foreign Application Priority Data

Jan. 21, 2021 (JP) ................................ 2021-007893

(51) Int. Cl.
*G16H 40/40* (2018.01)
*G06T 7/00* (2017.01)
(Continued)

(52) U.S. Cl.
CPC ........... *G16H 40/40* (2018.01); *G06T 7/0012* (2013.01); *G06T 7/50* (2017.01); *G06T 7/62* (2017.01);
(Continued)

(58) Field of Classification Search
CPC .. G16H 40/40; G06T 7/62; G06T 7/50; G06T 7/0012; G06T 2207/10024;
(Continued)

(56) References Cited

U.S. PATENT DOCUMENTS 7,602,963 B2 * 10/2009 Nightingale .......... G06T 7/0006
382/152
11,270,110 B2 * 3/2022 Kadambi ............. G06V 10/764
(Continued)

FOREIGN PATENT DOCUMENTS

JP 2005-122707 A 5/2005
JP 2011-86219 A 4/2011
(Continued)

OTHER PUBLICATIONS

International Search Report issued in corresponding International Application No. PCT/JP2021/038179 mailed Jan. 18, 2022 (4 pages).

*Primary Examiner* — Michael I Ezewoko
(74) *Attorney, Agent, or Firm* — Osha Bergman Watanabe & Burton LLP

(57) ABSTRACT

An information processing system includes: a memory that stores a medical device state model that indicates a state of a medical device corresponding to an external appearance of the medical device; and a processor that: acquires external appearance data indicating the external appearance of the medical device, analyzes reusability of the medical device, as the state of the medical device, using the medical device state model, and outputs medical device state information indicating an analyzed state of the medical device, the medical device state model indicating the reusability of the medical device as the state of the medical device.

14 Claims, 8 Drawing Sheets

(51) Int. Cl.
  *G06T 7/50* (2017.01)
  *G06T 7/62* (2017.01)
(52) U.S. Cl.
  CPC ............... *G06T 2207/10024* (2013.01); *G06T 2207/10081* (2013.01); *G06T 2207/20081* (2013.01); *G06T 2207/30004* (2013.01); *G06T 2207/30136* (2013.01)
(58) Field of Classification Search
  CPC . G06T 2207/10081; G06T 2207/20081; G06T 2207/30004; G06T 2207/30136
  See application file for complete search history.

(56) References Cited

U.S. PATENT DOCUMENTS

| | | | | |
|---|---|---|---|---|
| 11,715,558 | B2* | 8/2023 | Hameed | A61B 1/00029 600/118 |
| 12,086,701 | B2* | 9/2024 | Sjögren | G06V 20/698 |

FOREIGN PATENT DOCUMENTS

| | | | |
|---|---|---|---|
| JP | 6531213 | B1 | 6/2019 |
| JP | 6584721 | B1 | 10/2019 |

\* cited by examiner

FIG. 2

| TYPE | SITE | OUTER SHAPE |
|---|---|---|
| CATHETER | DISTAL END PORTION, TUBE PORTION | LONGITUDINAL DIRECTION SIDE SURFACE |
| GUIDE WIRE | DISTAL END PORTION, WIRE PORTION | LONGITUDINAL DIRECTION SIDE SURFACE |
| MANTLE TUBE | DISTAL END PORTION, TUBE PORTION | LONGITUDINAL DIRECTION SIDE SURFACE |
| ENDOSCOPE | DISTAL END PORTION, INSERTION PORTION | LONGITUDINAL DIRECTION SIDE SURFACE |
| FORCEPS | COUPLING PORTION, DISTAL END PORTION | MAIN SURFACE |
| SCALPEL | BLADE | SIDE SURFACE (FRONT AND BACK) |
| . . . | . . . | . . . |

FIG. 3

| SHAPE | STATE |
|---|---|
| SHAPE 01 | NORMAL |
| SHAPE 02 | SIGN |
| SHAPE 03 | ABNORMAL |

FIG. 4

| SHAPE/COLOR | STATE |
|---|---|
| SHAPE/COLOR 11 | NORMAL |
| SHAPE/COLOR 12 | SIGN |
| SHAPE/COLOR 13 | ABNORMAL |

FIG. 5

| DIAMETER DISTRIBUTION | STATE |
|---|---|
| DIAMETER DISTRIBUTION 21 | NORMAL |
| DIAMETER DISTRIBUTION 22 | SIGN |
| DIAMETER DISTRIBUTION 23 | ABNORMAL |

FIG. 6

| LENGTH | STATE |
|---|---|
| LENGTH 31 | NORMAL |
| LENGTH 32 | SIGN |
| LENGTH 33 | ABNORMAL |

FIG. 7

| SURFACE SHAPE | STATE |
|---|---|
| SURFACE SHAPE 41 | NORMAL |
| SURFACE SHAPE 42 | SIGN |
| SURFACE SHAPE 43 | ABNORMAL |

FIG. 8

| PATTERN | STATE |
|---|---|
| PATTERN 51 | NORMAL |
| PATTERN 52 | SIGN |
| PATTERN 53 | ABNORMAL |

FIG. 9

| LENGTH | STATE | GUIDANCE INFORMATION |
|---|---|---|
| LENGTH 31 | NORMAL | GUIDANCE INFORMATION 61 |
| LENGTH 32 | SIGN | GUIDANCE INFORMATION 62 |
| LENGTH 33 | ABNORMAL | GUIDANCE INFORMATION 63 |

FIG. 10

| SITE | FREQUENCY |
|---|---|
| SITE 71 | FREQUENCY 71 |
| SITE 72 | FREQUENCY 72 |
| SITE 73 | FREQUENCY 73 |

FIG. 11

| SURFACE SHAPE | STATE | REUSABILITY |
|---|---|---|
| SURFACE SHAPE 81 | NORMAL | ○ |
| SURFACE SHAPE 82 | SIGN | ○ |
| SURFACE SHAPE 83 | ABNORMAL 1 | △ |
| SURFACE SHAPE 84 | ABNORMAL 2 | × | under
INFORMATION PROCESSING SYSTEM, INFORMATION PROCESSING METHOD, AND NON-TRANSITORY COMPUTER READABLE MEDIUM

CROSS-REFERENCE TO RELATED APPLICATIONS

This application claims priority to Japanese Patent Application No. 2021-007893, filed on Jan. 21, 2021, the entire content of which is incorporated herein by reference.

TECHNICAL FIELD

The present disclosure relates to an information processing system, an information processing method, and a non-transitory computer readable medium. The present disclosure relates to, for example, a technology for maintaining and managing a medical device.

BACKGROUND ART

In a medical facility such as a hospital, various devices are used in medical practice such as treatment, diagnosis, care, and rehabilitation. In particular, it is important to manage the state of a device that directly or indirectly acts on a living body such as a human body in order to ensure a function and safety. The effectiveness of the medical practice and the protection of the living body are thus achieved. Conventionally, various methods have been proposed for a method of determining the state of a medical device.

For example, Patent Document 1 describes a failure prediction system including an inspection information processing device that processes information related to inspection using a medical device repeatedly used by performing cleaning, a first reading device that is communicable with the inspection information processing device and reads identification information of the medical device, a maintenance information processing device that processes information related to cleaning of the medical device, information related to maintenance of the medical device, and information related to failure of the medical device, a second reading device that is communicable with the maintenance information processing device and reads the identification information of the medical device, and an information management device. The information management device is communicable with the inspection information processing device and the maintenance information processing device and manages medical device management information including information regarding inspection, information regarding cleaning, information regarding maintenance, information regarding failure, a format of the medical device, and the like in association with identification information of the medical device. The information management device includes a failure predictor that performs machine learning of the information regarding inspection, the information regarding cleaning, the information regarding maintenance, the information regarding failure, and the medical device management information and predicts a failure possibility of the medical device.

Patent Document 2 describes a maintenance management method capable of collecting condition information related to a medical device installed in a medical facility, determining a maintenance work content of the medical device on the basis of the collected condition information, and providing information related to the determined maintenance work content to a person in charge of maintenance of the medical device. The maintenance management method is capable of acquiring condition information related to a medical device identified by designated device identification information, comparing the acquired condition information with predetermined reference information, determining work identification information for identifying a content of maintenance work determined according to a comparison result, and providing information related to the content of maintenance work identified by the determined work identification information to a person in charge of maintenance of the medical device identified by the device identification information. The predetermined reference information is updated on the basis of condition information at a failure of the medical device and condition information at a failure of another medical device of the same series as the medical device.

CITATION LIST

Patent Document

[Patent Document 1]
  Japanese Patent (Granted) Publication No. 6531213
[Patent Document 2]
  Japanese Unexamined Patent Application, First Publication No. 2005-122707

However, it is not always easy to visually determine the state of the medical device. It may take many years of experience and intuition to make an accurate determination. For example, there are various forms of damage to medical devices. The presence or absence of usability, the act that caused the damage, and the measure for making the medical device usable may differ for each form of damage. A user of a medical device may wish to comprehend signs preceding damage.

SUMMARY

The present disclosure has been provided in view of the above points, and one or more embodiments of the present disclosure provide an information processing system, an information processing method, and a non-transitory computer readable medium capable of accurately determining a state of a medical device.

(1) The present disclosure has been provided in view of the above points, and an aspect of the present disclosure is an information processing system including a memory that stores: a medical device state model that indicates a state of the medical device corresponding to an external appearance of the medical device; and a processor that: acquires external appearance data indicating the external appearance of the medical device, analyzes reusability of the medical device as the state of the medical device using the medical device state model, and outputs medical device state information indicating an analyzed state of the medical device, the medical device state model indicating the reusability of the medical device as the state of the medical device.

(2) Another aspect of the present disclosure is an information processing method comprising: acquiring external appearance data indicating an external appearance of a medical device; analyzing reusability of the medical device as the state of the medical device using a medical device state model that indicates a state of the medical device corresponding to the external appearance of the medical device, and outputting medical device state information indicating an analyzed state of the medical device, the medical device state model indicating the reusability of the medical device as the state of the medical device.

According to the present disclosure, it is possible to accurately determine a state of a medical device.

BRIEF DESCRIPTION OF DRAWINGS

FIG. 2 is a table illustrating a correspondence relationship between a site to be analyzed and an outer shape according to one or more embodiments.

FIG. 3 is a table illustrating a correspondence relationship between the shape and the state of the medical device according to one or more embodiments.

FIG. 4 is a table illustrating a correspondence relationship between a state and a combination of the shape and the color of the medical device according to one or more embodiments.

FIG. 5 is a table illustrating a correspondence relationship between the diameter distribution and the state of the medical device according to one or more embodiments.

FIG. 6 is a table illustrating a correspondence relationship between the length and the state of the medical device according to one or more embodiments.

FIG. 7 is a table illustrating a correspondence relationship between the surface shape and a state according to one or more embodiments.

FIG. 8 is a table illustrating a correspondence relationship between the state and the combination of the pattern and the color according to one or more embodiments.

FIG. 9 is a table illustrating a correspondence relationship between the state of a medical device and guidance information according to one or more embodiments.

FIG. 10 is a table illustrating frequency of abnormality for each site according to one or more embodiments.

FIG. 11 is a table illustrating a correspondence relationship between the surface shape and reusability according to one or more embodiments.

DETAILED DESCRIPTION OF EMBODIMENTS

Figure 1:
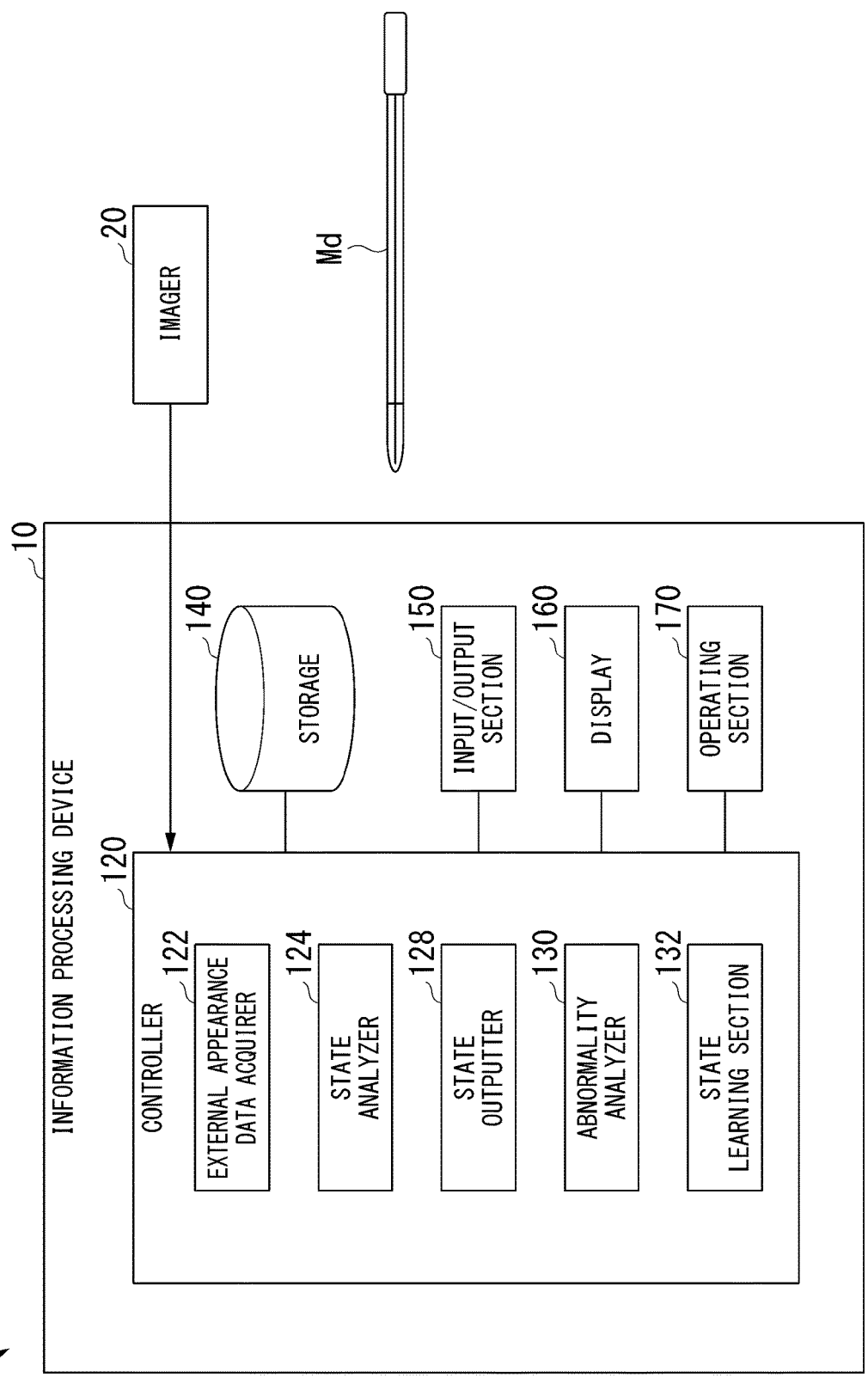
FIG. 1 is a schematic block diagram illustrating a functional constitution example of the information processing system according to one or more embodiments.

Hereinafter, embodiments of the present invention will be described with reference to the drawings. First, an outline of one or more embodiments will be described. FIG. 1 is a schematic block diagram illustrating a functional constitution example of the information processing system 1 according to one or more embodiments. The information processing system 1 includes an information processing device 10 and an imager 20.

The information processing device 10 acquires external appearance data indicating the external appearance of the medical device. In the example illustrated in FIG. 1, image data is input from the imager 20 as external appearance data. Medical device state model data indicating a relation between the external appearance of the medical device Md and the state of the medical device Md is set in the information processing device 10. The information processing device 10 uses the medical device state model data to analyze the state of the medical device Md indicated by the acquired external appearance data. The information processing device 10 outputs medical device state information indicating the analyzed state of the medical device Md. The information processing device 10 may be constituted as a general-purpose device such as a personal computer (PC), a workstation, or a server device, or may be constituted as a dedicated device.

The imager 20 captures an image of the external appearance of the medical device as a subject. The imager 20 generates external appearance data indicating the captured external appearance, and outputs the generated external appearance data to the information processing device 10. The imager 20 may be, for example, any of a camera, a scanner, and the like. The camera may be either a video camera that captures a moving image or a still camera that captures a still image. The camera includes an imaging element in which a plurality of light receiving elements that detects visible light, infrared light, or ultraviolet light emitted from a subject surface is arranged on a two-dimensional plane for each pixel. The camera may be a stereoscopic camera that captures a three-dimensional shape of a subject. The three-dimensional shape may be indicated by point cloud data indicating coordinate points distributed on the surface of the subject in the three-dimensional space or may be expressed by using a pixel value for each pixel on the two-dimensional plane and a distance or parallax from a point on the subject surface corresponding to each pixel.

The scanner may be either a three-dimensional scanner or a CT (Computed Tomography) scanner. The three-dimensional scanner includes a light source that irradiates a subject with visible light, infrared rays, or ultraviolet rays as incident waves, an imaging element formed by arranging a plurality of light receiving elements that detects reflected waves from a surface of the subject, and a light reception processor (not illustrated). The light reception processor determines the distance to the point on the surface of the corresponding subject for each pixel on the basis of the phase difference between the detected reflected wave and the known incident wave. Since the position of the imaging element depends on the relative direction with respect to the optical axis of the imaging element, the light reception processor can specify the position of the point on the basis of the distance determined for each pixel and the position of the pixel. The surface shape of the object is represented by a set of positions specified for each pixel.

A CT scanner includes a radiation source that irradiates an object with an X-ray as an incident wave, an X-ray sensor formed by arranging a plurality of detection elements that detects a transmitted wave transmitted from the object, and a detection processor. The detection processor calculates the amount of absorption of the X-ray for each site on the surface of the subject or inside the subject by simultaneously calculating the intensity of the transmitted wave detected for each detection element and the intensity of the known incident wave. The detection processor can generate an image representing the surface and internal structure of the subject by using the gradation of the pixel corresponding to the absorption amount for each site. The X-ray has relatively high permeability to an organic substance such as a polymer workpiece or a living body but has low permeability to a metal material. Examples of the metal material used in medical devices include stainless steel and a nickel-titanium alloy. Therefore, with respect to a device including a member composed of a metal material as a raw material, even in a state of being used for diagnosis or treatment or in a state in which biological tissue is attached, an image representing the external appearance of the device can be acquired by using the CT scanner.

Note that in the present application, the external appearance means a figure or an appearance that can be visually recognized and comprehended, and includes a concept that observation from the outside is not necessarily required. The imager 20 may be integrally constituted with another device that does not have imaging as a main function. The imager 20 may be, for example, a microscope, a magnifying glass, or an endoscope on which a camera or a scanner is mounted. The imager 20 may include, for example, an optical filter represented by a polarizing plate or a band pass filter. The imager 20 may calculate a shape characteristic value indicating a characteristic of the whole or a partial site of the subject and include the calculated shape characteristic value in the external appearance data. An example of the shape characteristic value will be described later.

In the present application, a medical device refers to a device used in contact with a part of a living body mainly in therapy, diagnosis, care, or rehabilitation for humans and other animals. The state of the medical device appears in the external appearance. The medical device may be, for example, any instrument such as a catheter, a guide wire, a mantle tube, an endoscope, forceps, a scalpel, or the like. Such medical devices tend to become significantly damaged due to repeated use and aging, and eventually become unsuitable for therapy, diagnosis, care, or rehabilitation. On the other hand, many experiences are required to accurately determine the state by visually observing the external appearance. In other words, it may be difficult for an inexperienced user of the medical device to correctly determine the state only by visually observing the external appearance. According to one or more embodiments, the user (for example, a medical practitioner, a patient, or a close relative of a patient) can know the state of the medical device Md by contacting the medical device state information indicating the state of the medical device Md analyzed from the external appearance data. The user is urged to continue using the normal medical device Md, and the use of the medical device Md in which the damage or the sign thereof appears is avoided.

Next, a constitution example of the information processing device 10 will be described. The information processing device 10 includes a controller (or computer) 120, a storage 140, an input/output section (or input/output device) 150, a display 160, and an operating section (or operating device) 170.

The controller 120 includes a hardware processor such as a central processing unit (CPU). The processor performs a function of the information processing device 10 by executing processing indicated by an instruction described in a predetermined program stored in advance in the storage 140. In the present application, executing a processing indicated by an instruction described in a program may be referred to as "executing the program", "executing the program", or the like. The controller 120 executes, for example, a program to implement the functions of an external appearance data acquirer 122, a state analyzer 124, a state outputter 128, an abnormality analyzer 130, and a state learning section 132. A functional constitution example of the controller 120 will be described later. Note that the controller 120 may be realized using a dedicated member.

The storage 140 stores various data used for processing executed by the controller 120. The storage 140 stores various data acquired by the controller 120. The storage 140 includes a storage medium such as a random access memory (RAM) and a read only memory (ROM).

The input/output section 150 inputs or outputs various types of data wirelessly or by wire with another device. The input/output section 150 may be connected to another device via a network. The input/output section 150 may include, for example, any one or both of an input/output interface, a communication interface, and the like.

The display 160 displays display information based on various display data input from the controller 120. The display 160 may be, for example, any of a liquid crystal display, an organic electroluminescence display, and the like.

The operating section 170 receives an operation on itself, generates an operation signal indicating various types of information instructed according to the received operation, and outputs the generated operation signal to the controller 120. The operating section 170 may include a general-purpose member such as a touch sensor, a mouse, or a keyboard, or may include a dedicated member such as a button or a knob. When the operating section 170 includes a touch sensor, the touch sensor may be integrated with a display constituting the display 160 to constitute a single touch panel.

Next, a functional constitution example of the controller 120 will be described. The external appearance data acquirer 122 acquires external appearance data from the imager 20. The external appearance data acquirer 122 stores the acquired external appearance data in the storage 140. The external appearance data may be input from another device via the input/output section 150 instead of the imager 20. The external appearance data is not limited to image data indicating a captured image and may be image data indicating an image synthesized using computer graphics.

The external appearance data may indicate a three-dimensional shape of the medical device as a subject. The three-dimensional shape may be significantly different in the shape observed depending on the viewpoint. Therefore, the external appearance data acquirer 122 may perform known viewpoint rendering processing on the acquired external appearance data and determine an image of a partial site representing a surface having a predetermined outer shape as a reference surface as an analysis target. For example, when the subject represented in the image is a catheter, a guide wire, an outer mantle tube, or an endoscope, the external appearance data acquirer 122 determines an image of a side surface parallel to the longitudinal direction and including a distal end portion as an analysis target (see FIG. 2). In a case where the subject is forceps, the external appearance data acquirer 122 determines a main surface on which a coupling portion constituting the forceps and a pair of distal end portions coupled using the coupling portion appear as an analysis target. In a case where the subject is a scalpel, the external appearance data acquirer 122 determines one or both side surfaces of the blade constituting the scalpel as an analysis target.

For example, in the viewpoint rendering processing, the external appearance data acquirer 122 repeats processing of collating a reference surface image representing a predetermined analysis target reference surface with a viewpoint image observed for each viewpoint and calculating an index value indicating the degree of coincidence between the reference surface image and the viewpoint image. The external appearance data acquirer 122 can search for a viewpoint that provides a viewpoint image that most matches the reference surface image by determining a viewpoint that provides the highest degree of coincidence with the calculated index value. In the storage 140, reference surface data indicating an image of a reference surface determined in advance for each type of medical device may be set in advance. The external appearance data acquirer 122 stores image data indicating an image of a site to be analyzed in the storage 140 as external appearance data. The image to be analyzed may be a two-dimensional image or a three-dimensional image.

The state analyzer 124 reads the external appearance data newly stored in the storage 140 and analyzes the state of the medical device represented in the external appearance data using the medical device state model data set in the storage 140 in advance with respect to the read external appearance data. For example, the state analyzer 124 determines an input value on the basis of the external appearance data and determines the state of the medical device using an output value calculated using a machine learning model for the determined input value. For example, the state analyzer 124 determines a signal value for each pixel indicated by the external appearance data as an input value input to the machine learning model. As a machine learning model, for example, a convolutional neural network (CNN) can be used. The medical device state model data is data indicating the state of the medical device corresponding to the external appearance of the medical device. The medical device state model data may include a parameter indicating a correspondence relationship between the external appearance of the medical device and the state of the medical device. The state analyzer 124 uses the parameter indicated by the medical device state model data as a parameter (in this application, it may be referred to as a "model parameter") of arithmetic processing based on the machine learning model.

The state analyzer 124 determines, as the state of the medical device, for example one of: normality; a sign of abnormality (in this application, it may be simply referred to as "sign"); and abnormality. Therefore, in the state analyzer 124, a stepwise value range is set for each stage divided into individual stages among the value ranges that can be taken as the output value. As the stepwise value range, for example, it is set to: 0.6 or more and 1 or less for abnormality; 0.3 or more and less than 0.6 for sign; and 0 or more and less than 0.3 for normality. The state analyzer 124 can specify the stepwise value range including the calculated output value and determine the degree of abnormality with respect to the specified stepwise value range. The degree of abnormality to be determined is not limited to three stages of normality, sign, and abnormality, and may be two stages or may be subdivided into four or more stages. The state analyzer 124 may adopt the calculated output value as the degree of abnormality. The state analyzer 124 stores the medical device state information indicating the determined state in the storage 140.

The state analyzer 124 may determine the type of abnormality for the whole or a partial site of the medical device as the characteristic of the abnormality (in the present application, it may be referred to as an "abnormality characteristic"). Types of abnormalities include, for example, tension, compression, bending, twisting, shearing, crushing, recession, chipping, swelling, constriction, wear, scratches, missing components, adhesion of foreign matters, and the like. The type of abnormality that can occur may vary depending on the type or site of the medical device. This is because conditions such as individual materials, shapes, directions of forces applied at the time of use, interference between members, and exposure to a drug or a living body, are different. For example, the type of abnormality with respect to the catheter includes abrasion of the distal end portion, crushing, tension, bending, twisting, shearing, scratching, melting, and the like of the tube portion. Types of anomalies of the guidewire include tension, bending, twisting, constriction, wear, scratch, corrosion, and the like.

The type of abnormality is classified into, for example, an abnormality due to a physical influence and an abnormality due to a chemical influence. Abnormalities due to physical effects include tension, compression, bending, twisting, shearing, crushing, recession, chipping, swelling, constriction, wear, scratches, missing components, adhesion of foreign matters, and the like. Examples of the abnormality due to a chemical influence include corrosion, melting, dissolution, and burning.

Therefore, in the medical device state model data, a candidate of the type of the abnormality to be determined may be associated in advance with a determination item that is one of the type and the site of the medical device or a combination thereof. By using such medical device state model data, the state analyzer 124 can determine the type of abnormality according to any determination unit of the type and the site of the medical device or a determination unit to be combined. The number of sites as a determination unit for one medical device may be two or more. The state analyzer 124 may determine the degree of abnormality for each abnormality type candidate. The state analyzer 124 may analyze a plurality of types of abnormality as candidates for one medical device or site. The state analyzer 124 may set the machine learning model so that the output value with respect to the input value can be calculated for each determination unit.

The state analyzer 124 may determine a characteristic of an external appearance (in the present application, may be referred to as "external appearance characteristics") in the whole or a partial site of the medical device indicated by the external appearance data, and analyze the state of the medical device with respect to external appearance characteristic information indicating the determined external appearance characteristic. The state of the medical device obtained by the analysis may include an abnormality characteristic. The medical device state model data may include a model parameter indicating a correspondence relationship between the external appearance characteristic information and the abnormality characteristic information. For example, the state analyzer 124 determines a characteristic value indicating the property of any one of the shape, the color, and the dimension in the whole or a partial site of the medical device or a combination of these characteristic values as the external appearance characteristic value indicating the external appearance characteristic.

A partial site of the medical device indicated by the external appearance data may be a predetermined member essential for exerting the function of the medical device or may be a joint portion formed by joining a plurality of predetermined members to each other. Since the positional relationship of the bonded portion changes while the plurality of members are in contact with each other by use, deformation and friction tend to be more significant than other sites. Any one or both of the shape and the dimension may change due to the deformation. Friction may cause a change in color tone.

The characteristic value indicating the shape is not limited to one indicating the characteristic of the two-dimensional shape, and one indicating the characteristic of the three-dimensional shape may be used. The characteristic value indicating the shape is mainly used for analyzing an abnormality characteristic due to a physical influence. The characteristic value indicating color may be any of: a set of luminosity and chromaticity; a hue; a set of luminosity and chroma; and the like. These characteristic values are derived from a color signal value for each data sample for a site to be analyzed constituting the external appearance data. The color signal value may be a value based on any color system such as an RGB value or a CMYK value. A representative value of the color signal value at the site may be used as a characteristic value indicating color. This is effective for analyzing abnormality characteristics due to a chemical influence. The characteristic value indicating color may be used instead of the characteristic value indicating the shape or may be used together with the characteristic value indicating the shape.

As a specific example of the medical device, with respect to the electrode catheter, the electrode and the catheter shaft mainly inserted into the body can be the analysis target site mainly for color. For the catheter shaft, states such as a change in color tone due to bending or friction, peeling or fading of the marker, discoloration due to burning of the energized portion, and the like are analyzed. The energized portion corresponds to a member where electricity is transmitted. The energized portion corresponds to, for example, an electrode of an electrode catheter, a counter electrode plate exposed on a surface, and the like.

The characteristic value indicating the shape corresponds to the above-described shape characteristic value. As the shape characteristic value, for example, a diameter, a diameter distribution, and the like at a predetermined reference position can be used for an elongated-shaped member such as a tube portion or a guide wire of a catheter. As the reference position, for example, a portion in contact with another member (for example, a distal end portion, a proximal end portion, and the like) or a portion having a significant shape change with use can be applied. The diameter distribution means a distribution of the diameter in the longitudinal direction. As a numerical value indicating a color, a representative value such as an average value or a mode value of color signal values for each pixel included in a portion indicating an individual member can be used. As the characteristic value indicating the dimension (in the present application, may be referred to as a "dimensional characteristic value"), for example, a length in the longitudinal direction with respect to the elongated-shaped member can be used. The state analyzer 124 may adopt a part of the shape characteristic values indicated in the external appearance data as one or both of the shape characteristic value and the dimensional characteristic value indicating the external appearance characteristic.

The dimensional characteristic value can also be used mainly for analysis of abnormality characteristics due to physical influence. Note that the portion having a significant shape change with use corresponds to a joint portion where a plurality of members is connected to each other, a portion in contact with a human body, a portion gripped by a user during operation, an electrode used for detecting or applying an electric signal, and the like. For example, a bending operating section or a rotation operating section for inserting a distal end of an elongated member such as a catheter or an endoscope into a human body, an electrode attached to the distal end, a marker representing an insertion site in external appearance, and the like are applicable.

The state analyzer 124 calculates the output value using the model parameter indicated by the medical device state model data based on the machine learning model, using the predetermined external appearance characteristic value as an input value instead of or together with the signal value for each pixel. The state analyzer 124 estimates abnormality characteristic information on the basis of the calculated output value.

The state outputter 128 reads the medical device state information newly stored in the storage 140, and outputs the read medical device state information to the display 160. The display 160 displays the medical device state information input from the state outputter 128. The state outputter 128 generates display data indicating any one of a character, a figure, a symbol, or a pattern indicating the state of the medical device indicated in the read medical device state information, or a predetermined combination, and outputs the generated display data to the display 160.

The abnormality analyzer 130 reads the medical device state information accumulated in the storage 140 and specifies any one of the site and the state (abnormality characteristic) of the medical device indicated by the read individual medical device state information or a combination thereof (in this application, it may be referred to as a "counter") as an analysis target item. The abnormality analyzer 130 determines the number counted for each item as a frequency (abnormality analysis). The abnormality analyzer 130 stores abnormality analysis information indicating the counted frequency in the storage 140. In counting the frequency, the abnormality analyzer 130 may use all the medical device state information accumulated in the storage 140 but may use only a part thereof. The abnormality analyzer 130 may use the medical device state information generated within a predetermined period (for example, one month to one year) up to the time point (current time point) for abnormality analysis and may not use the medical device state information in other periods. In the abnormality analyzer 130, a larger coefficient may be set in advance at a time point closer to the current time point, a coefficient corresponding to the time point may be specified for each piece of the medical device state information, and the specified coefficient may be added for each counter indicated by the medical device state information to be determined as the occurrence frequency. As a result, the frequency in which the state occurred at a time point closer to the current time point in the abnormality analysis is emphasized is obtained.

Note that the abnormality analyzer 130 may start (trigger) counting of frequencies when an operation signal indicating an abnormality analysis instruction is input from the operating section 170 or from another device via the input/output section 150.

The abnormality analyzer 130 may output and display the abnormality analysis information on the display 160. The abnormality analyzer 130 may output the abnormality analysis information to another device that is an input source of the operation signal via the input/output section 150.

The frequency may be represented by a cumulative value of the number of counts or the coefficient or may be represented by a normalized value normalized to fall within a predetermined value range (for example, 0 or more and 1 or less) for each counter. In addition, the frequency for each counter may be represented by the frequency of abnormality among the frequencies of the states of the individual medical devices.

FIG. 10 illustrates the abnormality analysis information. The exemplified abnormality analysis information indicates the frequency 71, the frequency 72, and the frequency 73 for each of the site 71, the site 72, and the site 73 as counters. Therefore, the user in contact with the abnormality analysis information can comprehend the site where the abnormality frequently occurs. In addition, the abnormality analysis information may be associated with medical device state information indicating the state of the medical device. Such abnormality analysis information is useful for analysis of an abnormality, and furthermore, maintenance management, development, and the like of a medical device.

The state learning section 132 acquires training data including a plurality of data sets including external appearance data indicating the external appearance of an existing medical device and state data indicating the state of the medical device in association with each other and generates medical device state model data using the acquired training data. The state learning section 132 determines an input value on the basis of the external appearance data, and determines a model parameter so that an output value calculated for each determination unit using a machine learning model with respect to the input value is as close as possible as the entire training data to a target value representing a state indicated by the state data corresponding to the training data for each data set (model learning). For example, the model parameters in the CNN include a convolution coefficient for an input value from a previous layer to a node belonging to a convolution layer and a fully connected layer, a bias value for the node and a parameter of an activation function, and necessity of reference to an input value from a node of a previous layer of the convolution layer.

In the model learning, the state learning section 132 sequentially updates the model parameters until convergence such that the magnitude of the difference between the target value and the output value for each determination unit calculated using the machine learning model with respect to the input value becomes smaller. When the amount of change in the model parameters before and after the update or the amount of change in the magnitude of the difference before and after the update is less than a predetermined convergence determination threshold, it can be determined that the model parameters have converged. As the index value of the magnitude of the difference, for example, an error function such as a sum of squared differences (SSD) or a cross entropy error can be used. The method for determining the model parameter may be any one of steepest descent, stochastic optimization, back-propagation, and the like. The state learning section 132 stores data indicating the calculated model parameters in the storage 140 as medical device state model data.

The state learning section 132 can use a method similar to that of the state analyzer 124 as a method of determining an input value from the external appearance data. The state learning section 132 sets a setting value corresponding to the degree of abnormality for each determination unit as an output value representing the state indicated by the state data. For example, in a case where the degree of abnormality is determined in two stages of "normality" and "abnormality", the state learning section 132 sets output values for the determination of "normality" and "abnormality" to 0 and 1, respectively. In a case where the degree of abnormality is determined in three stages of "normality", "sign", and "abnormality", the state learning section 132 sets output values for the determination of "normality", "sign", and "abnormality" to 0, 0.45, and 1, respectively. The value of 0.45 corresponds to the median value of the graded range given for "signs". When the degree of abnormality is determined in four stages, the state learning section 132 sets the output values for the determination of "normality" and "abnormality" to 0 and 1, respectively, and sets the output value for an intermediate stage other than these determinations to the median value of the stepwise value range for the intermediate stage.

Note that, in one or more embodiments, the machine learning model is not limited to a convolutional neural network (CNN) and may be any of a recurrent neural network (RNN) and a residual network (ResNet). The machine learning model is not limited to the neural network and may be a mathematical model such as a decision tree, a regression tree, or a support vector machine (SVM).

The state learning section 132 may acquire training data from another device and calculate model parameters using the acquired training data.

Next, an example of the correspondence relationship between the external appearance and the state indicated by the medical device state model data will be described. FIGS. 3 to 6 exemplify any one of a shape, a color, and a dimension, or a combination of any one of the shapes, the color, and the dimension as external appearance characteristics to be analyzed. The external appearance characteristic value indicating the external appearance characteristic may be explicitly given as an input value to the machine learning model, or external appearance data indicating an image of the whole or a partial site of the medical device as a subject having the external appearance characteristic may be given as an input value. As the input value, an external appearance characteristic value indicated in the external appearance data may be used, or an external appearance characteristic value of a predetermined medical device or a site may be determined from an image indicated in the external appearance data. Accordingly, the medical device state model data implicitly indicates the correspondence exemplified below.

FIG. 3 illustrates a correspondence between a shape and a state. In the example illustrated in FIG. 3, the state is given as normality, sign, or abnormality for the shape 01, the shape 02, and the shape 03 respectively. "01", "02", "03", and the like are codes for identifying individual information, and do not indicate numerical values.

FIG. 4 illustrates a correspondence relationship between a combination of a shape and a color and a state. In the example illustrated in FIG. 4, the state is given as normality, sign, or abnormality for the shape/color 11, the shape/color 12, and the shape/color 13 respectively.

FIG. 5 illustrates a correspondence relationship between the diameter distribution and the state. In the example illustrated in FIG. 5, the state is given as normality, sign, or abnormality for the diameter distribution 21, the diameter distribution 22, and the diameter distribution 23 respectively.

FIG. 6 illustrates a correspondence between a length and a state. In the example illustrated in FIG. 6, the state is given as normality, sign, or abnormality for the length 31, the length 32, and the length 33 respectively.

The state analyzer 124 may analyze the surface shape as the external appearance characteristic in place of or in addition to any of the shape, color, and dimension as the property of the medical device or any combination thereof. In the properties of the medical device, the surface shape means irregularities (for example, embossing) appearing on the surface, perforations (for example, a through hole such as a balloon catheter), or distribution thereof. The surface shape may represent a type of anomaly, such as wear, scratches, corrosion, melting, dissolution, etc., which can cause the equipment to fail to function. In addition, this type of abnormality tends to occur more significantly in some sites than in other sites. As the surface shape, for example, the guide wire has a surface shape of a rope pattern on the surface. This is because the guide wire is formed by twisting a plurality of fine wire materials in parallel. In the forceps, a plurality of fine grooves is cut in parallel to the longitudinal direction of each distal end portion on a surface (relative surface) on which a pair of distal end portions face each other. For a member constituted of metal as a material, the state analyzer 124 can analyze a state of the member by processing external appearance data indicating an image captured using X-rays at a stage where the medical device to be analyzed is used.

The surface shape can also be regarded as a combination of the three-dimensional shape of the surface and the pattern applied to the surface. The pattern corresponds to a distribution of color tone. The color tone includes luminosity (brightness) and saturation (color shade) as elements. The state analyzer 124 may analyze a pattern expressed in the two-dimensional space instead of the surface shape expressed in the three-dimensional space as the external appearance characteristics. The state analyzer 124 may calculate external appearance characteristic values indicating the periodicity of these patterns and use the calculated external appearance characteristic values as input values.

FIG. 7 illustrates a correspondence relationship between the surface shape and the state. In the example illustrated in FIG. 7, the state is given as normality, sign, or abnormality for the surface shape 41, the surface shape 42, and the surface shape 43 respectively.

FIG. 8 illustrates a correspondence relationship between a combination of a pattern and a color and a state. In the example illustrated in FIG. 8, the state is given as normality, sign, or abnormality for the pattern 51, the pattern 52, and the pattern 53 respectively.

The state outputter 128 may specify guidance information corresponding to the state of the medical device indicated by the read medical device state information, and output the specified guidance information to the display 160 in association with the medical device state information. In the storage 140, guide data indicating guide information regarding handling of the medical device is stored in advance for each state of the medical device. For example, in the example illustrated in FIG. 9, as states respectively corresponding to the length 31, the length 32, and the length 33, guidance information 61, guidance information 62, and guidance information 63 are given to normality, sign, and abnormality respectively. Therefore, in a case where the medical device to be analyzed has an external appearance characteristic of the length 33, the state analyzer 124 determines that the state of the medical device is abnormal. The state outputter 128 outputs the medical device state information indicating the abnormality and the guidance information 63 to the display 160 or another device in association with each other.

The guidance information may include, for example, information indicating usage for the determined state (in this application, it may be referred to as usage information). The usage information includes information indicating usage of the medical device for eliminating or reducing the abnormality. More specifically, the usage information includes, for example, any one or a combination of any one of a site to be held, an operation amount, an operation direction, timing, and the like. The usage information may further include information indicating usage of the medical device that tends to cause or promote abnormality. As a result, the user who has contact with the usage information is urged to recognize the usage of the medical device that tends to generate or promote the abnormality and to adopt the usage of the medical device for eliminating or reducing the abnormality. One or more embodiments can be applied to education, training, and the like for measures using medical equipment such as surgery.

Note that the guidance information may include, for example, maintenance management information (maintenance information) for the determined state. The maintenance management information includes information indicating a measure for eliminating or reducing the abnormality, a measure for delaying the progress of the abnormality, or a measure for prohibiting the use of the medical device with respect to any one or a combination of the determined type, site, and degree of the abnormality. More specifically, for example, any one of or a combination of replacement, cleaning, polishing, surface processing, disposal of a member, and a request for an action to a predetermined provider such as a vendor, a manufacturer, or a maintenance and management provider of the medical device can be cited.

The guidance information may be expressed using any one of characters, symbols, patterns, images, and the like, or any combination thereof. The image may be any one of a still image and a moving image, or a combination thereof.

The use of the medical device is often limited to only one time in order to ensure hygiene and safety for the living body and may be discarded after use (disposable). However, due to the growing environmental issues, growing public health concerns, reduction in medical costs, differences from foreign laws, and the like, reuse may be achieved multiple times. Aspects of reuse include, but are not limited to, as they are, or as a result of user routine measures such as cleaning and disinfection, and where some components are collected and used as new products. An aspect of reuse may vary depending on the type or member of the medical device.

The concept of reuse may cover use on another patient, use on the same patient at another time, and multiple uses in an action such as one surgery, medication, or examination.

Therefore, the state analyzer 124 may use the external appearance data to analyze the reusability of the medical device represented in the external appearance data. The reusability means whether or not reuse is possible, or a degree thereof. As the degree of reusability, the magnitude of the load required for reuse may be used. Any one or a combination of labor, cost, time, and the like may be used as the load required for reuse. The determination unit of the reusability may be the entire medical device or a part thereof. The state analyzer 124 may analyze the reusability in a case where the state of the whole or a partial site of the medical device is determined to be abnormal and may not analyze the reusability in a case where the state is determined to be normal.

The state analyzer 124 can calculate an output value indicating the degree of reusability with respect to an input value determined on the basis of the external appearance data by using a machine learning model by using a method similar to the analysis of the abnormality characteristic and determine the reusability on the basis of the calculated output value. The state analyzer 124 includes information indicating the determined reusability (in this application, it may be referred to as "reusability information") in the medical device state information and stores the medical device state information in the storage 140. The state outputter 128 may output display data indicating the reusability information to the display 160 or may output the display data to another device via the input/output section 150. It is possible to assist a user who has come in contact with the reusability information in determining the reusability.

The state learning section 132 can acquire a model parameter for determining the reusability by performing model learning with the reusability of the entire or partial site of the medical device as a determination unit using a method similar to the model parameter used for analysis of the abnormality characteristic. When constituting the training data used for model learning, the state learning section 132 includes an output value indicating the reusability in association with the external appearance data in the data set included in the training data. The state learning section 132 can determine the output value according to the degree of reusability using the same method as the degree of abnormality.

FIG. 11 illustrates a correspondence between the surface shape and the reusability. In the example illustrated in FIG. 11, the states are given as normality, sign, abnormality 1, and abnormality 2 for the surface shape 81, the surface shape 82, the surface shape 83, and the surface shape 84 respectively. Abnormality 2 has a more significant degree of abnormality than abnormality 1. The reusability is given as ○, ○, Δ, and × for normality, sign, abnormality 1, and abnormality 2 respectively. ○, Δ, × indicate reusable, reusable with condition, and unreusable, respectively. The reusable condition includes, for example, a condition in which a special measure involving a load exceeding a daily measure is applied to enable the use, a condition in which a part of members is replaced to enable the use, a condition in which a predetermined contractor such as a maintenance contractor is requested to perform the measure, and the like. Information indicating these conditions may be included in the guidance information.

Note that a user skilled in handling a medical device may consider that the state indicated by the medical device state information displayed on the display 160 or another device as an output destination is different from the state determined by himself/herself. Therefore, the operating section 170 or another device may generate an operation signal indicating the state of the determination unit determined by the user according to the received operation and output the operation signal to the state learning section 132. An operation signal indicating the state of the determination unit may be input to the state learning section 132 from another device via the operating section 170 or the input/output section 150, and a data set in which state data indicating the state of the determination unit and external appearance data indicating the external appearance of the medical device to be determined are associated with each other may be added to the training data. The state learning section 132 may update the model parameters by performing model learning (transfer learning) on the training data to which the data set is newly added. The state learning section 132 stores the medical device state model data indicating the updated model parameters in the storage 140 instead of the existing medical device state model data.

A user (reusability judge) who determines the reusability may consider that the displayed reusability information is different from the reusability determined by himself/herself. The operating section 170 or another device may generate an operation signal indicating the reusability information using all or a part of the medical device determined by the user as a determination unit according to the operation received from the user and output the operation signal to the state learning section 132. An operation signal indicating the reusability information may be input to the state learning section 132 from another device via the operating section 170 or the input/output section 150, and a data set in which state data indicating the reusability of the determination unit and external appearance data indicating the external appearance of the medical device to be determined are associated with each other may be added to the training data. The state learning section 132 may update the model parameters by performing model learning on the training data to which the data set is newly added. The state learning section 132 stores the medical device state model data indicating the updated model parameters in the storage 140 instead of the existing medical device state model data.

Figure 12:
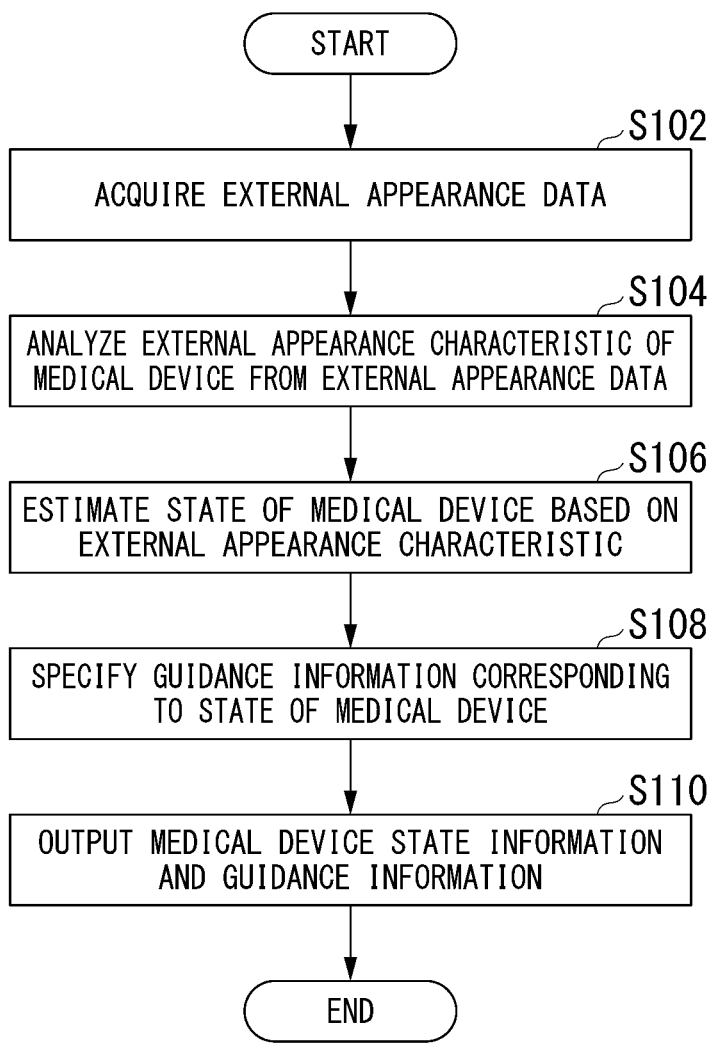
FIG. 12 is a flowchart illustrating a first example of medical device state information provision processing according to one or more embodiments.

Next, an example of information processing according to one or more embodiments will be described. FIG. 12 is a flowchart illustrating a first example of the medical device state information provision processing according to one or more embodiments.

(Step S102) The external appearance data acquirer 122 of the information processing device 10 acquires external appearance data indicating the external appearance of the medical device.

(Step S104) The state analyzer 124 analyzes the external appearance characteristic of the medical device using the acquired external appearance data.

(Step S106) The state analyzer 124 estimates the state of the medical device using the machine learning model for the analyzed external appearance characteristic.

(Step S108) The state outputter 128 specifies guidance information corresponding to the estimated state of the medical device.

(Step S110) The state outputter 128 outputs the medical device state information indicating the estimated state of the medical device and the specified guidance information in association with each other to the display 160 of the own device or another device which is the output destination device. Thereafter, the processing of FIG. 12 is terminated.

Figure 13:
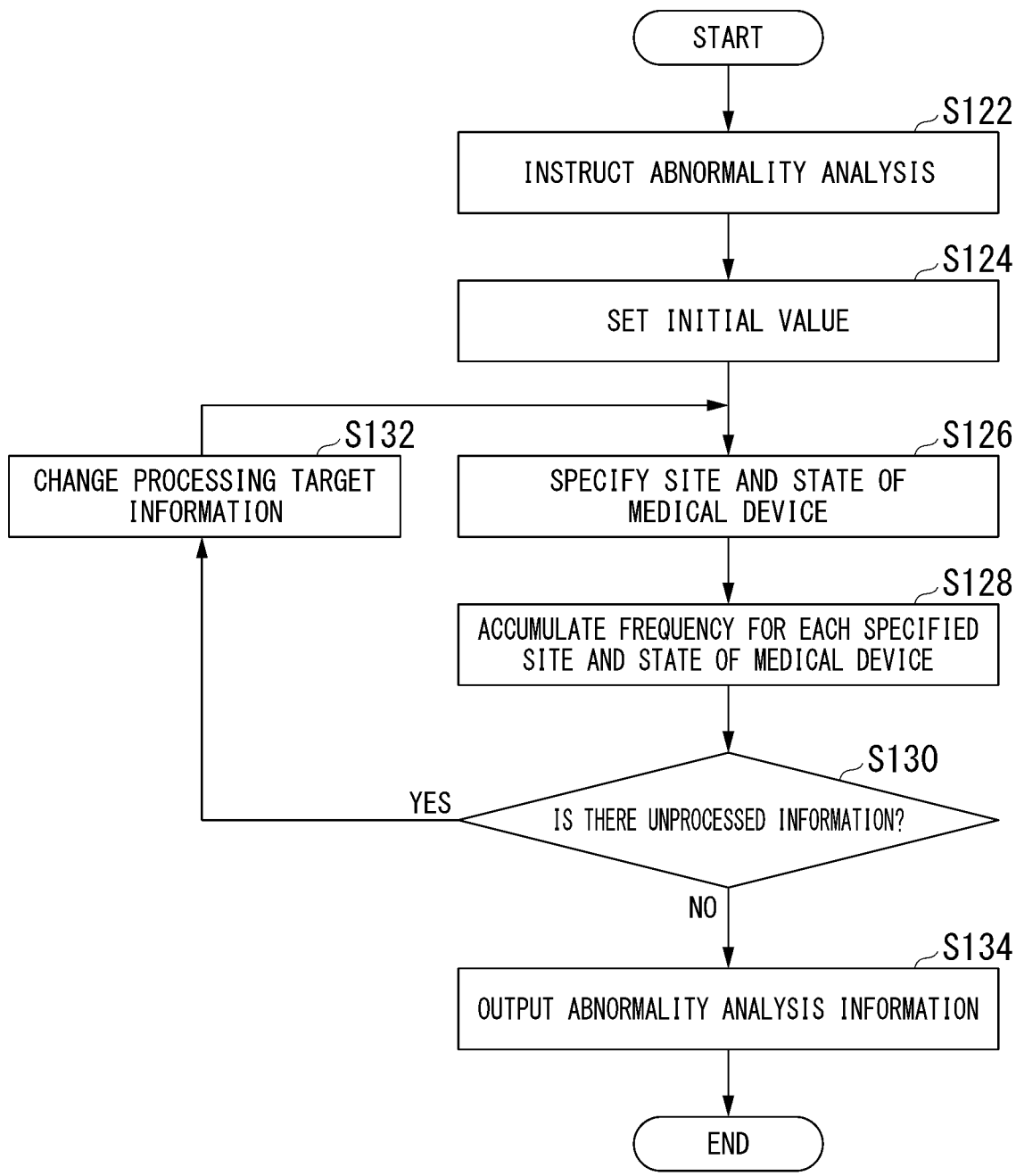
FIG. 13 is a flowchart illustrating an example of abnormality analysis processing according to one or more embodiments.

Next, an example of information processing according to one or more embodiments will be described. FIG. 13 is a flowchart illustrating an example of abnormality analysis processing according to one or more embodiments.

(Step S122) The abnormality analyzer 130 of the information processing device waits for an input of an operation signal indicating an abnormality analysis instruction from the operating section 170 of the own device or from another device and proceeds to the processing of Step S124 when the operation signal is input.

(Step S124) The abnormality analyzer 130 sets (initializes) a predetermined initial value. The abnormality analyzer sets zero as an initial value of the frequency for each counter.

(Step S126) The abnormality analyzer 130 specifies, as a counter, any one of a site (or the entire medical device), a state, or a combination as a counter from the medical device state information within the predetermined analysis period.

(Step S128) The abnormality analyzer 130 accumulates (increments) the frequency by adding a predetermined increment (for example, 1) to the frequency of the specified counter.

(Step S130) The abnormality analyzer 130 determines the presence or absence of unprocessed medical device state information within a predetermined analysis period. When the presence is determined (Step S130 YES), the processing proceeds to Step S132. When the absence is determined (Step S130 NO), the processing proceeds to Step S134.

(Step S132) The abnormality analyzer 130 changes the medical device state information to be processed to unprocessed medical device state information. Thereafter, the abnormality analyzer 130 executes the processing of steps S 126 and S 128 on the changed medical device state information.

(Step S134) The abnormality analyzer 130 outputs the abnormality analysis information indicating the frequency of each counter to the display 160 of the own device as an input source of the abnormality analysis instruction or to another device via the input/output section 150.

Figure 14:
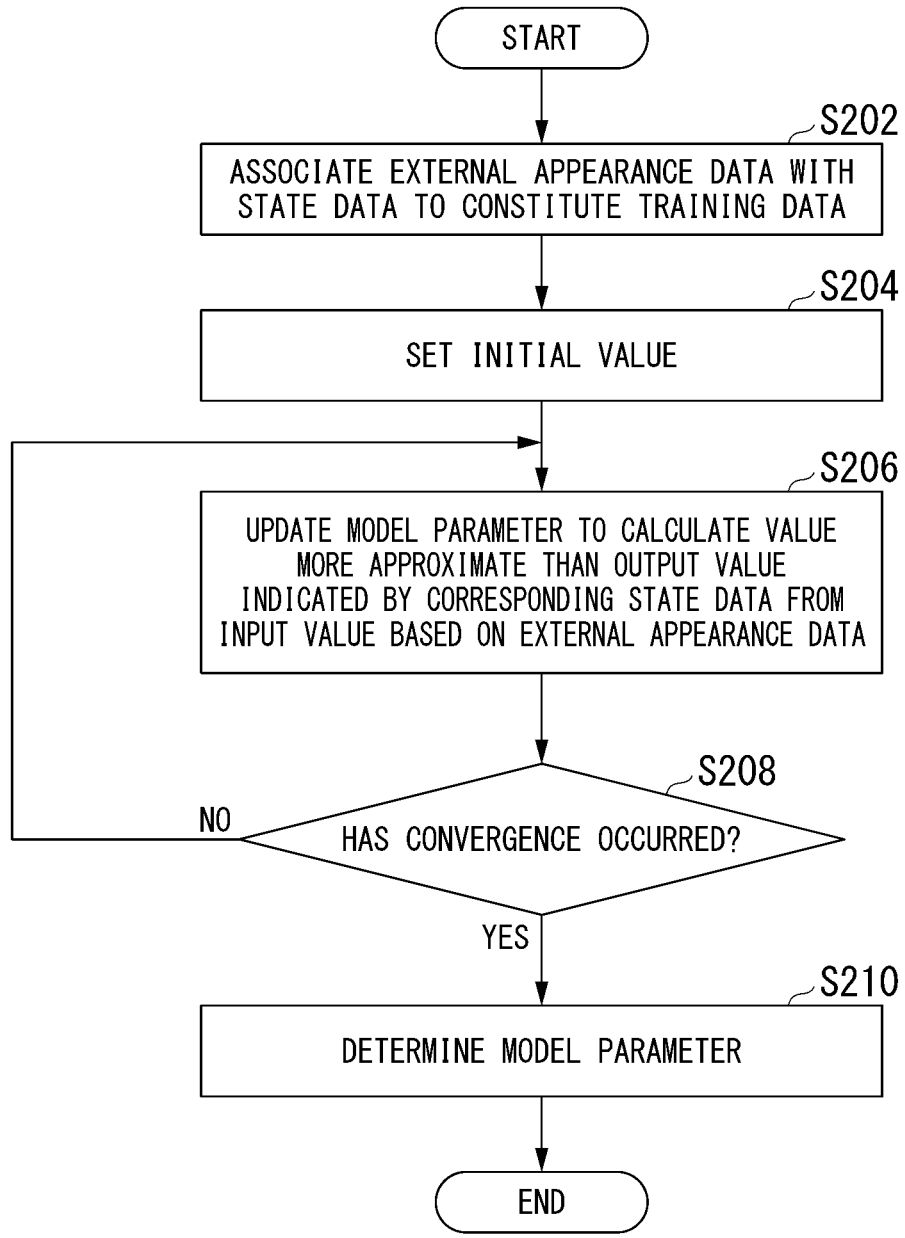
FIG. 14 is a flowchart illustrating an example of model learning processing according to one or more embodiments.

FIG. 14 is a flowchart illustrating an example of the model learning processing according to one or more embodiments.

(Step S202) The state learning section 132 collects external appearance data indicating the external appearance of the medical device and state data indicating the state of the medical device. The state learning section 132 constitutes a data set by associating state data indicating a state of a medical device whose external appearance data indicates external appearance with each collected external appearance data. The state learning section 132 constitutes training data including a plurality of sets of constituted data sets.

(Step S204) The state learning section 132 sets initial values of model parameters of the machine learning model. The initial value may be a predetermined arbitrary value or a value of an existing model parameter.

(Step S206) The state learning section 132 determines an input value to the machine learning model from the external appearance data for each data set, and recursively updates the model parameter of the machine learning model so that an arithmetic value calculated using the machine learning model for the determined input value further approximates an output value representing a state indicated by the state data of the data set.

(Step S208) The state learning section 132 determines whether or not the model parameters to be updated have converged. When it is determined that convergence has occurred (Step S208 YES), the processing proceeds to Step S210. When it is determined that convergence has not occurred (Step S208 NO), the processing of Step S206 is repeated.

(Step S210) The state learning section 132 determines the model parameters obtained at that time as model parameters to be used for estimation of the state of the medical device and stores the medical device state model data indicating the determined model parameters in the storage 140.

Figure 15:
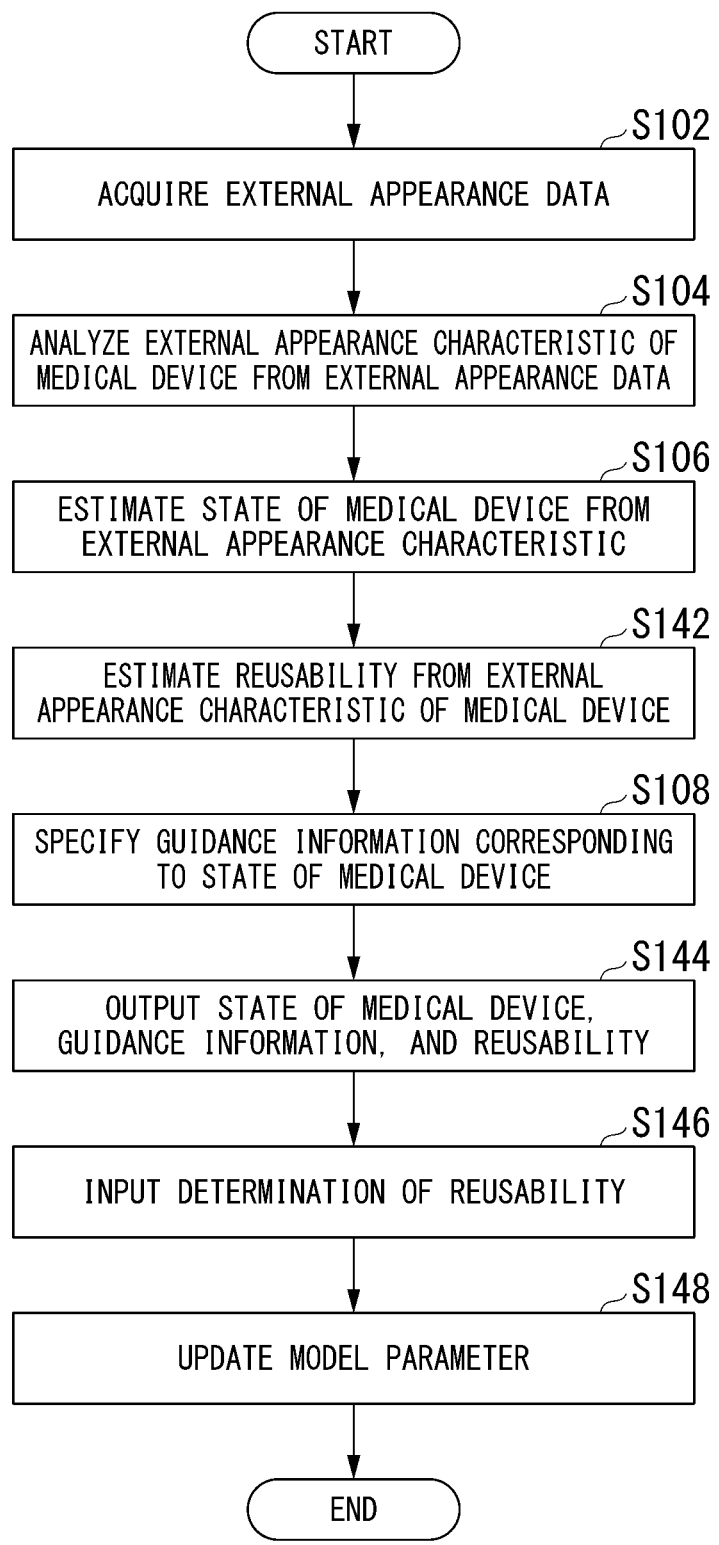
FIG. 15 is a flowchart illustrating a second example of the medical device state information provision processing according to one or more embodiments.

FIG. 15 is a flowchart illustrating a second example of the medical device state information provision processing according to one or more embodiments. The processing illustrated in FIG. 15 includes processing in steps S 102 to S 108 and processing in steps S 142 to S 148. Since steps S 102 to S 108 are similar to the processing illustrated in FIG. 12, the description thereof is incorporated. After Step S106 is completed, the processing proceeds to Step S142.

(Step S142) The state analyzer 124 estimates the reusability of all or a part of the medical device using the machine learning model for the analyzed external appearance characteristic. Thereafter, the processing proceeds to Step S108. After Step S108 is completed, the processing proceeds to Step S144.

(Step S144) The state outputter 128 includes the reusability information indicating the estimated reusability in the medical device state information indicating the estimated state of the medical device, and outputs the specified guidance information to the display 160 of the own device or to another device which is the output destination device in association with each other.

(Step S146) The state learning section 132 waits for an input of an operation signal indicating the reusability determined by the user from the operating section 170 of the own device or from another device.

(Step S148) The state learning section 132 defines an output value indicating the reusability transmitted by the input operation signal and forms a data set by associating state data indicating the defined output value with external appearance data obtained by analyzing the external appearance characteristic. The state learning section 132 updates the model parameters of the machine learning model using the training data including the formed data set. Thereafter, the processing of FIG. 15 is terminated.

Note that FIG. 15 illustrates a case where the processing of steps S 106, S 142, and S 108 is executed in that order, but the present invention is not limited thereto. The processing in Step S142 may be executed before Step S106 or after Step S108.

As described above, the information processing device 10 according to one or more embodiments includes the external appearance data acquirer 122, the state analyzer 124, and the state outputter 128. The external appearance data acquirer 122 acquires external appearance data indicating the external appearance of the medical device. The state analyzer 124 analyzes the state of the medical device indicated by the external appearance data using the medical device state model data indicating the state of the medical device corresponding to the external appearance of the medical device. The state outputter 128 outputs medical device state information indicating the analyzed state of the medical device.

According to this constitution, a state corresponding to the external appearance of the medical device is determined. Unlike the determination by visual observation, the state is determined objectively and stably. By avoiding use of a medical device in which damage or other abnormality has occurred, a risk due to the abnormality can be reduced.

The external appearance data may be data indicating the three-dimensional shape of the medical device. The external appearance data acquirer 122 may determine a site representing a predetermined outer shape from the three-dimensional shape indicated by the external appearance data as a state analysis target.

According to this constitution, the site representing the outer shape to be analyzed is fixed. Generally, the three-dimensional shape has a different outer shape observed depending on the position of the viewpoint, but by making the site constant, the determination accuracy of the state of the medical device based on the external appearance can be improved and stabilized.

The medical device state model data may be data indicating a correspondence relationship between external appearance characteristic information indicating an external appearance characteristic that is at least one of a shape, a color, and a dimension in at least a partial site as an external appearance of the medical device and abnormality information indicating at least one characteristic of a type and a degree of abnormality of the medical device as a state of the medical device.

The state analyzer 124 may analyze the characteristic of the abnormality of the medical device according to the external appearance characteristic of the medical device based on the external appearance data as the state of the medical device.

According to this constitution, the characteristic of the abnormality according to the external appearance characteristic determined based on the external appearance data is analyzed. Therefore, the user can learn the analyzed characteristics of the abnormality and can take measures corresponding to the learned characteristics of the abnormality.

The external appearance characteristic may include at least one of a shape, a color tone, and a dimension of a joint portion between a plurality of members constituting the medical device. The state analyzer 124 may analyze characteristics of the abnormality according to the property.

According to this constitution, the characteristic of the abnormality according to the property in the joint portion determined based on the external appearance data is analyzed.

The external appearance characteristic may include a diameter of a predetermined member of the medical device. The state analyzer 124 may analyze the characteristics of the abnormality according to the diameter distribution.

According to this constitution, the characteristic of the abnormality according to the distribution of the diameter of the predetermined member determined based on the external appearance data is analyzed.

The external appearance characteristic may include the length of a predetermined member of the medical device. The state analyzer 124 may analyze characteristics of the abnormality according to the length.

According to this constitution, the characteristic of the abnormality corresponding to the length of the predetermined member determined based on the external appearance data is analyzed.

The external appearance characteristic may include a surface shape of a predetermined member of the medical device. The state analyzer 124 may analyze the characteristics of the abnormality in the surface shape.

According to this constitution, the characteristic of the abnormality according to the surface shape of the predetermined member determined based on the external appearance data is analyzed.

The external appearance characteristic may include a pattern on the surface of a predetermined member of the medical device. The state analyzer 124 may analyze characteristics of the abnormality according to the pattern.

According to this constitution, the characteristic of the abnormality according to the pattern of the surface of the predetermined member determined based on the external appearance data is analyzed.

The predetermined member may have a metal material. The external appearance data acquirer 122 may acquire image data indicating an image captured using the X-ray sensor as the external appearance data.

Since the X-rays are transmitted through the organic compound and are not transmitted through the metal, the external appearance of a predetermined member is captured in the captured image, and images of other members constituted of a polymer compound and a biological tissue are not captured. According to this constitution, even when the medical device is used, the state is analyzed based on the external appearance of the predetermined member having the metal material.

The state outputter 128 may determine guidance information corresponding to the analyzed state of the medical device from preset guidance information regarding handling of the medical device for each state of the medical device.

According to this constitution, the guidance information according to the state of the medical device is determined. The user who has come in contact with the fixed guidance information is urged to handle the guidance information. In addition, it is possible to train a user having poor use experience about handling of the medical device.

The information processing device 10 may include an abnormality analyzer 130 that analyzes the frequency of abnormality for each counter that is at least one item of the site and the state of the medical device.

According to this constitution, the frequency of the abnormality generated for each counter is analyzed. The user having contact with the analyzed frequency can know one or both of the site where the abnormality frequently occurs and the type of the abnormality. As a result, the user can use the obtained information for maintenance or development of the medical device.

The medical device state model data may include the reusability of the medical device as the state of the medical device. The state analyzer 124 may analyze the reusability of the medical device indicated by the external appearance data.

According to this constitution, the reusability of the medical device corresponding to the external appearance of the medical device is determined. An objective and stable determination of reusability is made. By avoiding the use of a medical device that cannot be reused, it is possible to avoid the use of a medical device that cannot be reused while pursuing economic efficiency and environmental load reduction by reuse.

The information processing device 10 may further include a state learning section 132 that generates medical device state model data using training data including a data set in which external appearance data indicating the external appearance of the medical device and state data indicating the state of the medical device are associated with each other.

According to this constitution, the medical device state model data can be generated using the external appearance data acquired by the own device and the training data including the state data corresponding to the external appearance data. Since the medical device state model data corresponding to the use environment of the own device is obtained, the state of the medical device can be estimated more accurately.

The state learning section 132 may include, in the training data, a data set in which the external appearance data acquired by the external appearance data acquirer 122 is associated with the state data acquired from the output destination device that has output the medical device state information.

According to this constitution, the medical device state data is updated using the data set in which the state data indicating the state of the medical device determined by the user who uses the output destination device is associated with the external appearance data to be analyzed. The medical device state data is updated such that the correspondence relationship between the external appearance and the state of the medical device matches the external appearance indicated in the external appearance data and the state determined by the user. Therefore, the estimated state can be brought close to the state determined by the user.

Although the embodiments of the present invention has been described in detail with reference to the drawings, the specific constitution is not limited to the above, and various design changes and the like can be made without departing from the gist of the present invention.

For example, the information processing device 10 may function as a server device that receives external appearance data from each of one or a plurality of imagers 20 via the input/output section 150 and processes the received external appearance data. The state outputter 128 may output the medical device state information to another device via the input/output section 150 instead of the display 160 or together with the display 160. The other device may be, for example, a terminal device of a user of the medical device to be analyzed. The terminal device may be, for example, an information device such as a personal computer, a tablet terminal device, or a multifunctional mobile phone. In the storage 140, user data indicating the imager 20 as a transmission source of the external appearance data and another device as an output destination of the medical device state information may be stored in advance. The state outputter 128 can specify the other device corresponding to the transmission source of the external appearance data as the output destination of the medical device state information with reference to the user data. The input/output section 150 may be connected to the imager 20 or another device so as to be able to transmit and receive various data using a network.

The information processing device 10 includes the imager 20 and may be constituted as a single information processing device or the information processing system 1. In the information processing device 10, one or both of the display 160 and the operating section 170 may be omitted. One or both of the display 160 and the operating section 170 are separate from the information processing device 10 and may be connected wirelessly or by wire via the input/output section 150.

In the controller 120, one or both of the abnormality analyzer 130 and the state learning section 132 may be omitted.

In addition, a part or all of the information processing device 10 in the above-described embodiments may be realized as an integrated circuit such as a large-scale integration (LSI). Each functional block of the information processing device 10 may be individually formed into a processor, or some or all of the functional blocks may be integrated into a processor. In addition, the circuit integration method is not limited to LSI, and may be realized by a dedicated circuit or a general-purpose processor. In addition, in a case where an integrated circuit technology replacing the LSI has appeared due to the progress of the semiconductor technology, an integrated circuit according to the technology may be used.

INDUSTRIAL APPLICABILITY

According to the information processing system, the information processing method, and the non-transitory computer readable medium of each of the above aspects, a state corresponding to the external appearance of the medical device is determined. Unlike the determination by visual observation, the state is determined objectively and stably. By avoiding use of a medical device in which damage or other abnormality has occurred, a risk due to the abnormality can be reduced.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

10 Information processing device
20 Imager
120 Controller
122 External appearance data acquirer
124 State analyzer
128 State outputter
130 Abnormality analyzer
132 State learning section
140 Storage
150 Input/output section
160 Display
170 Operating section

What is claimed is:

1. An information processing system comprising:
a storage that stores:
medical device state information; and
a medical device state model that indicates:
a state of a medical device corresponding to an external appearance of the medical device, and
reusability of the medical device corresponding to the state of the medical device; and
a processor that:
extracts, from the storage, the medical device state information,
computes a frequency of abnormality in the medical device state information,
acquires, with an imager, external appearance data indicating the external appearance of the medical device,
identifies, as an input to the medical device state model, portion data indicating a portion where the frequency of abnormality is higher than other portions out of the external appearance data,
specifies the reusability of the medical device corresponding to the state of the medical device, using the portion data as the input to the medical device state model, and
displays the medical device state information including the state of the medical device, wherein
the external appearance data indicate a three-dimensional shape of the medical device, and
the processor further:
identifies, as the portion, a site representing a predetermined outer shape from the three-dimensional shape,
presets coefficients for the medical device state information, wherein
each of the coefficients is larger for a time closer to a current time, and
computes the frequency of abnormality by accumulating the coefficients within a predetermined period up to the current time.

2. The information processing system according to claim 1, wherein
the medical device state model indicates a correspondence relation between external appearance characteristic information and abnormality information, wherein
the external appearance characteristic information indicates, as the external appearance of the medical device, an external appearance characteristic that is at least one of: a shape; a color; and a dimension in the portion of the medical device, and
the abnormality information indicates, as the state of the medical device, a characteristic of at least one of a type and a degree of an abnormality of the medical device, and
the processor analyzes, as the state of the medical device, a characteristic of abnormality of the medical device depending on the external appearance characteristic of the medical device based on the external appearance data.

3. The information processing system according to claim 2, wherein
the external appearance characteristic includes at least one property among a shape, a color tone, and a dimension of a joint portion between a plurality of members constituting the medical device; and the processor analyzes the characteristic of abnormality depending on the property.

4. The information processing system according to claim 2, wherein
the external appearance characteristic includes a diameter of a predetermined member of the medical device, and
the processor analyzes the characteristic of abnormality depending on a distribution of the diameter.

5. The information processing system according to claim 2, wherein
the external appearance characteristic includes a length of a predetermined member of the medical device, and
the processor analyzes the characteristic of abnormality depending on the length.

6. The information processing system according to claim 2, wherein
the external appearance characteristic includes a surface shape of a predetermined member of the medical device, and
the processor analyzes the characteristic of abnormality depending on the surface shape.

7. The information processing system according to claim 2, wherein
the external appearance characteristic includes a surface pattern of a predetermined member of the medical device, and
the processor analyzes the characteristic of abnormality depending on the surface pattern.

8. The information processing system according to claim 6, wherein
the predetermined member is composed of a metal material, and
the processor acquires, as the external appearance data, image data indicating an image captured using an X-ray sensor.

9. The information processing system according to claim 1, wherein
the processor determines, based on preset guidance information regarding handling of the medical device with respect to the state of the medical device, guidance information depending on the analyzed state of the medical device.

10. The information processing system according to claim 1, wherein
the processor analyzes the frequency of abnormality for at least one item among the portion of the medical device and the state of the medical device.

11. The information processing system according to claim 1, wherein
the processor learns the medical device state model using training data that include a plurality of data sets each including a relationship between the external appearance data and state data indicating the state of the medical device.

12. The information processing system according to claim 11, wherein
the processor includes, in the training data, a data set including the relationship between the external appearance data and the state data acquired from an output destination device.

13. A non-transitory computer readable medium storing instructions causing a computer to execute:
storing:
medical device state information; and
a medical device state model that indicates:
a state of a medical device corresponding to an external appearance of the medical device, and
reusability of the medical device corresponding to the state of the medical device;
extracting, from the storage, the medical device state information;
computing a frequency of abnormality in the medical device state information;
acquiring, with an imager, external appearance data indicating the external appearance of the medical device,
identifying, as an input to the medical device state model, portion data indicating a portion where the frequency of abnormality is higher than other portions out of the external appearance data,
specifying the reusability of the medical device corresponding to the state of the medical device, using the portion data as the input to the medical device state model, and
displaying the medical device state information including the state of the medical device, wherein
the external appearance data indicate a three-dimensional shape of the medical device, and
the computer further executes:
identifying, as the portion, a site representing a predetermined outer shape from the three-dimensional shape,
presetting coefficients for the medical device state information, wherein
each of the coefficients is larger for a time closer to a current time, and
computing the frequency of abnormality by accumulating the coefficients within a predetermined period up to the current time.

14. An information processing method comprising:
storing:
medical device state information; and
a medical device state model that indicates:
a state of a medical device corresponding to an external appearance of the medical device, and
reusability of the medical device corresponding to the state of the medical device;
extracting, from the storage, the medical device state information;
computing a frequency of abnormality in the medical device state information;
acquiring, with an imager, external appearance data indicating an external appearance of the medical device;
identifying, as an input to the medical device state model, portion data indicating a portion where the frequency of abnormality is higher than other portions out of the external appearance data,
specifying the reusability of the medical device corresponding to the state of the medical device, using the portion data as the input to the medical device state model, and
displaying the medical device state information including the state of the medical device, wherein
the external appearance data indicate a three-dimensional shape of the medical device, and
the method further includes:
identifying, as the portion, a site representing a predetermined outer shape from the three-dimensional shape,
presetting coefficients for the medical device state information, wherein
each of the coefficients is larger for a time closer to a current time, and computing the frequency of abnormality by accumulating the coefficients within a predetermined period up to the current time.

\* \* \* \* \*